Nov. 20, 1962 D. H. MOREY, JR Plant Pat. 2,194
ROSE PLANT
Filed Jan. 8, 1962
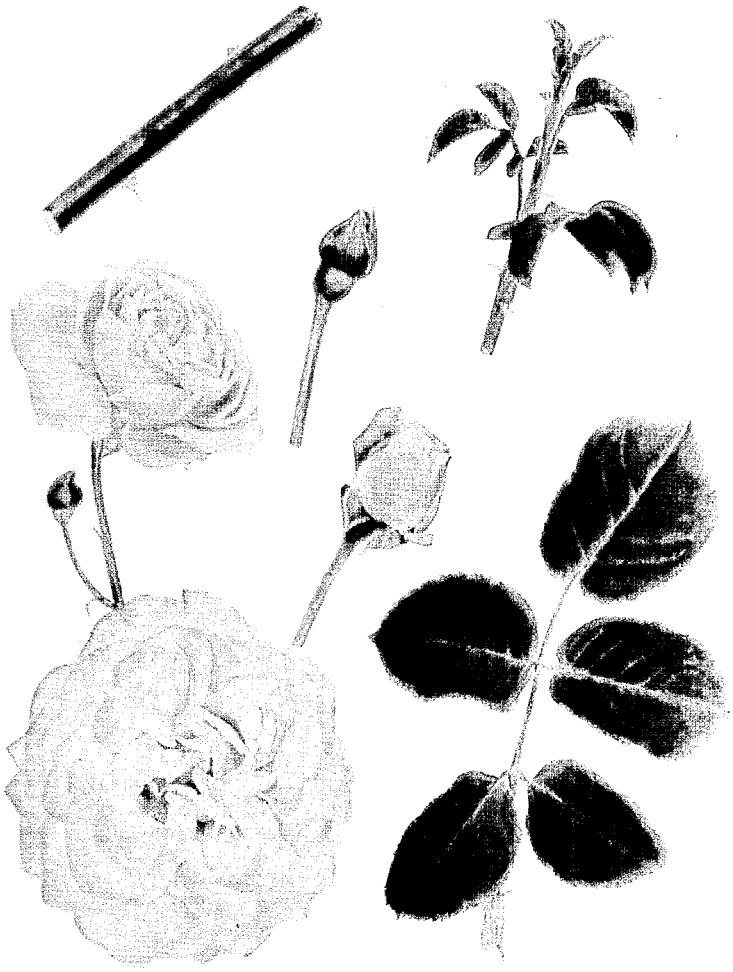
Inventor.
Dennison H. Morey, Jr.
By: Robb & Robb
Attorneys.

United States Patent Office

Plant Pat. 2,194
Patented Nov. 20, 1962

2,194
ROSE PLANT

Dennison H. Morey, Jr., Pleasanton, Calif., assignor to Jackson & Perkins Company, Newark, N.Y., a corporation of New York Filed Jan. 8, 1962, Ser. No. 165,052
1 Claim. (Cl. 47—61)

The present invention relates to a new and distinct variety of rose plant of the climber class, which was originated by me by crossing the hybrid tea variety known as "Lavender Queen" (unpatented) with the floribunda variety known as "Amy Vanderbilt" (Plant Patent No. 1,585).

The primary objective of this breeding was to produce a new rose variety of the climber class which bears flowers of lavender color. This objective was fully achieved, along with other desirable features which contribute to the novelty and distinctiveness of my new variety, as evidenced by the following unique combination of characteristics which are outstanding therein and which distinguish it from its parents, as well as from all other varieties of which I am aware:

(1) A habit of bearing flowers of medium size (approximately 3 inches in diameter) in clusters which bloom throughout the spring and summer;

(2) A strong Old Rose Perfume flower fragrance; and (3) A distinctive and attractive flower color corresponding to Daphne Pink, lightly overcast with Magenta, which is quite unusual in climbing roses.

Asexual reproduction of my new variety by budding, as performed at Pleasanton, California, and also at Newark, New York, shows that the foregoing characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with Ridgway's Color Standards and Nomenclature:

Parentage: Seedling.
*Seed parent.*—"Lavender Queen."
*Pollen parent.*—"Amy Vanderbilt."

Classification:
*Botanic.*—Climber.
*Commercial.*—Climber.

*Flower*

(Observations made from specimens grown outdoors at Newark, New York, during the early morning in the early part of the month of September.)

Blooming habit: Recurrent—intermittent.

Bud:
*Size.*—Medium.
*Form.*—Ovoid; is not affected by wet or hot weather.
*Color.*—When sepals first divide—Rosolane Purple, Plate 26. When petals begin to unfurl—Amaranth Purple, Plate 12. When half-blown: inside of petals—Liseran Purple, Plate 26, lightly overcast with Magenta, Plate 26 on edge of petal; reverse of petals—Spinel Red, Plate 26, lightly overcast with Rosolane Purple, Plate 26.
*Sepals.*—Slightly branched; curl back when petals begin to unfurl. Color: inside—Rinnemann's Green, Plate 18; outside—Bice Green, Plate 17.
*Calyx.*—Color—Bice Green, Plate 17. Shape—pear. Size—small. Aspect—smooth. Odor when rubbed—none.

*Peduncle.*—Length — medium. Aspect — rough. Strength—erect; slender. Color—Parrot Green, Plate 6.
*Opening.*—Opens up well; is not affected by adverse weather conditions.

Bloom:
*Size.*—Medium. Average size when fully expanded—3 inches.
*Borne.*—In rounded clusters.
*Stems.*—Medium length; strong.
*Form (when first open).*—Cupped. Permanence—retains its form to the end, but outer petals curl back.
*Petalage.*—Double (full but open center). Number of petals under normal conditions—from 35 to 40.
*Color.*—Center of flower—Liseran Purple, Plate 26, overcast with Magenta, Plate 26 on the outer edge of the petals. Outer petals—Eupatorium Purple, Plate 38, with outer edge lightly overcast with Light Perilla Purple, Plate 37. Base of petals (aiglet)—Pinard Yellow, Plate 4. Inside of petals—Daphne Pink, Plate 38, lightly overcast with Magenta, Plate 26. Reverse of petals—Light Rosolane Purple, Plate 26, lightly overcast with Deep Rose Pink, Plate 12. General tonality from a distance—Daphne Pink, Plate 38, lightly overcast with Magenta, Plate 26.
*Discoloration.*—General tonality at end of first day—Daphne Pink, Plate 38, lightly overcast with Magenta, Plate 26. Second day—Daphne Pink, Plate 38, lightly overcast with Magenta, Plate 26. Third day—Eupatorium Purple, Plate 38, with outer edge slightly overcast with Light Perilla Purple, Plate 37.

Petals:
*Texture.*—Thick; is not affected by wet or hot weather.
*Appearance.*—Inside—satiny. Outside—shiny.
*Form.*—Oval.
*Arrangement.*—Imbricated (regularly arranged shingle-like); quartered.
*Petaloids in center.*—Few; small.
*Persistence.*—Drop off cleanly.
*Fragrance.*—Strong. Nature—"Old Rose Perfume" (centifolia).
*Lasting quality.*—On the plant—long. As cut flower—long.

*Genital Organs*

Stamens, anthers: Medium size; few; arranged regularly around styles. Color—Olive-Ocher, Plate 30.
Stamens, filaments (threads): Medium length. Color—Barium Yellow, Plate 16.
Pollen: Color—Ivory Yellow, Plate 30.
Styles: Bunched; uneven length; short; thin.
Stigmas: Color—Light Chalcedony Yellow, Plate 17.
Ovaries: All enclosed in calyx.
Hips: None.
Seeds: None.

*Plant*

Form: Climber.
Growth: Vigorous; upright; branching.
Foliage: Compound of 3–5 leaflets.
*Size.*—Large.
*Quantity.*—Abundant.
*Color.*—New foliage: upper side—Oxblood Red, Plate 1; under side—Mineral Red, Plate 27. Old foliage: upper side—Dark Cress Green, Plate 31; under side—Bice Green, Plate 17.
*Shape.*—Oval.
*Texture.*—Upper side — leathery. Under side—smooth.

*Ribs and veins.*—Prominent.
*Edge.*—Serrated (saw toothed).
Serration.—Both double and single; small.
*Leaf stem.*—Color—Courge Green, Plate 17. Under side—smooth.
*Stipules.*—Medium length; smooth.

Wood:
*New wood.*—Color—Oil Green, Plate 5. Bark—smooth.
*Old wood.*—Color—Varley's Green, Plate 18. Bark—smooth.

Thorns:
*Thorns.*—Quantity: on main stalks from base—ordinary; on laterals from stalk—ordinary. Form—narrow base; medium length; hooked downward. Color (when young)—Eugenia Red, Plate 13. Position—irregular.

*Prickles.*—Quantity: on main stalks—none; on laterals—none.
*Short needles.*—Quantity: on main stalks—none; on laterals—none.

I claim:

A new and distinct variety of rose plant of the climber class, substantially as herein shown and described, characterized particularly as to novelty by the unique combination of a habit of bearing flowers of medium size in clusters which bloom throughout the spring and summer seasons, a strong Old Rose Perfume flower fragrance, and a distinctive, attractive and unusual general color tonality of the flowers, corresponding to Daphne Pink, lightly overcast with Magenta.

No references cited.